United States Patent [19]

Cisco et al.

[11] 4,204,916
[45] May 27, 1980

[54] PROCESS FOR RECOVERING ACID CHLORIDES BY DISTILLATION

[75] Inventors: Thomas F. Cisco, Ardsley; George E. Hansen, Yorktown Heights, both of N.Y.; Robert N. Agate, Freehold, N.J.

[73] Assignee: Stauffer Chemical Company, Westport, Conn.

[21] Appl. No.: 866,138

[22] Filed: Dec. 30, 1977

[51] Int. Cl.² .............................................. B01D 3/34
[52] U.S. Cl. .......................................... 203/6; 203/8; 203/52; 549/78
[58] Field of Search ................................... 203/6, 7–9, 203/38, 52, 57, 20, 68, 70; 260/332.2 A, 332.2 C; 544/28; 549/78

[56] References Cited

U.S. PATENT DOCUMENTS

| 2,884,359 | 4/1959 | Bloom et al. ............................ 203/52 |
| 2,884,363 | 4/1959 | Bloom et al. ............................ 203/57 |
| 3,129,224 | 4/1964 | Collins ............................ 260/332.2 A |
| 3,220,935 | 11/1965 | Nations et al. ..................... 260/544 D |
| 3,409,510 | 11/1968 | LeMaster et al. ...................... 203/57 |
| 3,467,581 | 9/1969 | Privette et al. ......................... 203/52 |
| 3,763,023 | 10/1973 | Horsley ................................... 203/63 |

OTHER PUBLICATIONS

Product Information Sheet, "Silicone Fluids SWS–101" from SWS Silicone Corp.

Primary Examiner—Wilbur L. Bascomb, Jr.
Attorney, Agent, or Firm—Michael E. Zall

[57] ABSTRACT

A process for recovering an acid chloride from a mixture containing the same, consisting of distilling the acid chloride from the mixture in the presence of an effective quantity of a distillation improvement additive, such as an organo polysiloxane or a mineral oil, which remains substantially liquid under the conditions of distillation.

7 Claims, 1 Drawing Figure

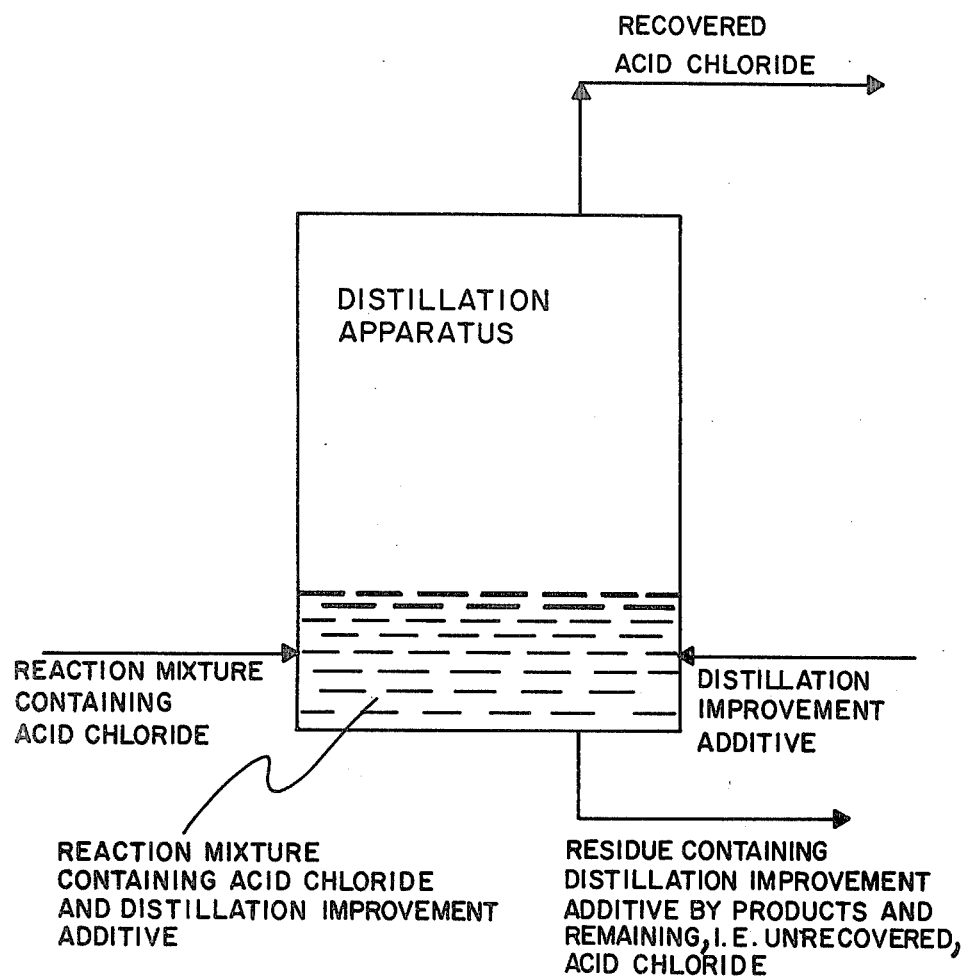
FIGURE

PROCESS FOR RECOVERING ACID CHLORIDES BY DISTILLATION

BACKGROUND OF THE INVENTION

1. Field of the Invention

This invention relates to an improvement in processes for the production of acid chlorides and more particularly to a process for recovering acid chlorides from mixtures containing the same.

2. Description of the Prior Art

The acid chlorides with which this invention is primarily concerned are known intermediates in the production of antimicrobial compounds such as 3-methyl-7-aminodecephalosporanic acid derivatives, see U.S. Pat. No. 3,129,224. The entire disclosure of this patent is incorporated herein by reference.

Generally, an acid is reacted with a chlorinating agent to produce a reaction mixture containing the desired acid chloride. This reaction mixture is then purified by distillation either continuously or batchwise, preferably under vacuum at a low temperature to prevent degradation.

During the above-described chlorination and distillation processes, by-products, polymers and degradation products are produced which cause a decrease in yield of the desired acid chloride. In particular, the acid chlorides are sensitive to temperature and tend to degrade and/or polymerize when subjected to excessive temperatures for long periods of time such as those encountered in distillation. The resultant degradation products can foul heat transfer surfaces. In order to overcome this problem, it has been proposed to recover the acid chlorides from the reaction mixture by the use of wiped and thin film evaporators; however, these evaporation devices are expensive to use and operate, and fouling of the equipment and residue removal can be a problem.

It is an object of this invention to provide an improved method for recovering acid chlorides from mixtures containing the same.

It is another object of this invention to recover acid chlorides from reaction mixtures at increased yields.

SUMMARY OF THE INVENTION

The foregoing and other objects are accomplished by a process for recovering an acid chloride from a mixture containing the same, comprising distilling the acid chloride from the mixture in the presence of an effective quantity of a distillation improvement additive which remains substantially liquid under the conditions of distillation.

BRIEF DESCRIPTION OF DRAWING

The FIGURE is a schematic representation of the process of this invention showing a distillation apparatus. The apparatus has a feed stream of reaction mixture containing acid chloride and a feed stream of distillation improvement additive. Recovered acid chloride and residue streams leave the apparatus. A reaction mixture containing acid chloride and distillation improvement additive is contained in the apparatus.

DESCRIPTION OF THE PREFERRED EMBODIMENTS

Preferably, the process is used for recovering acid chlorides having the structure:

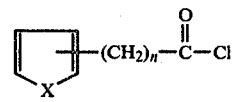

wherein X is a divalent oxygen or divalent sulfur atom, and n has the value 0, 1, 2, or 3.

The preferred mixture from which the acid chloride is recovered is a reaction mixture produced by the chlorination of an acid having the structure:

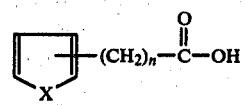

with a chlorinating agent.

Preferred chlorinating agents are thionyl chloride ($SOCl_2$), phosphorus trichloride ($PCl_3$), and phosphorus pentachloride ($PCl_5$). A particularly preferred chlorinating agent is thionyl chloride. Thionyl chloride is preferred due to the fact that the products formed (except for the acid chloride) are gases and can be relatively easily separated from the reaction mixture, and any excess thionyl chloride can be removed from the reaction mixture by distillation.

Examples of acid chlorides which may be recovered in accordance with the process of this invention are acid chlorides of the following acids:
alpha-thienylacetic acid;
beta-thienylacetic acid;
alpha-thienylcarboxylic acid;
beta-thienylcarboxylic acid;
alpha-furylcarboxylic acid;
beta-furylcarboxylic acid;
alpha-furylacetic acid;
beta-furylacetic acid;
2-(beta-thienyl)-propionic acid; and
3-(alpha-furyl)-propionic acid.

Preferably, the acid chloride is distilled from the reaction mixture in the presence of an effective quantity of a distillation improvement additive of organo polysiloxane or mineral oil which remains substantially liquid under the conditions of distillation.

The process of this invention has been found to enable recovering of increased yields of the desired acid chloride and to enable recovering said chlorides from residues hitherto discarded.

The mechanism by which the instant process achieves these desired results is not definitely understood. It is believed, however, that the liquid distillation improvement additive employed herein may (1) act as a heat exchange medium preventing polymerization and/or degradation of the acid chlorides; or (2) function as a fluidizing medium for the by-products allowing more complete distillation of the acid chloride. The mechanism may be in accordance with either of these mechanisms or both.

The selection of the distillation improvement additive depends to a large extent on the particular acid chloride being recovered. It is essential that the distillation improvement additive remains substantially liquid under the conditions of distillation, i.e., have a low volatility at the temperature and pressure of distillation.

Taking into consideration the equipment and process utilized, the distillation improvement additive is selected so that the quantity of vaporized additive found in the distilled acid chloride is kept below an allowable level which makes the distilled acid chloride useless or undesirable for its intended purpose. This allowable level is dependent on the particular acid chloride produced, the type distillation improvement additive utilized, the subsequent process steps performed on the acid chloride, and the particular use to which the final product (for which the acid chloride is an intermediate) is to be used.

Additionally, the distillation improvement additive should not polymerize and/or degrade at the temperatures and pressures of distillation. It is highly desirable that the distillation improvement additive be insoluble in the particular acid chloride produced and the by-products of the reaction so that, upon completion of the distillation, the additive may be phase separated from the by-products and the remaining acid chloride and reused. Optionally, upon completion of the distillation, the residue containing the additive by-products and remaining acid chloride can be distilled to separate the additive for reuse. The residue containing the additive can also be disposed of, but for economic reasons this may be undesirable.

Particularly preferred distillation improvement additives are organo polysiloxanes and mineral oils.

The organo polysiloxanes which may be employed in carrying out the instant invention and their methods of manufacture are well-known in the art as disclosed, for example, in U.S. Pat. Nos. 2,384,384; 2,398,187; and 2,604,469; the entire disclosures of these patents are incorporated herein by reference. In general, these polysiloxanes are organo-silicon polymers which comprise essentially silicon atoms connected to each other by oxygen atoms and organic radicals attached through carbon-silicon linkages to the silicon atoms. They may be cyclic but preferably linear in character, and their recurring unit of structure may be represented by the formula:

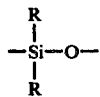

wherein the R's represent organic radicals such as alkyl, alicyclic, aryl, alkaryl, aralkyl, and alkenyl. Preferably, dimethyl polysiloxanes are used in this invention because of their greater stability. It is particularly preferred that linear dimethyl polysiloxanes terminated with nonreactive trimethyl siloxy groups be utilized. Preferred organo polysiloxanes are the SWS-101 silicone fluids from SWS Silicone Corporation, Adrian, Michigan. A particularly preferred silicone fluid is SWS-101 (50).

Mixtures of organo polysiloxanes can be employed as a distillation improvement additive. Generally, organo polysiloxanes are always mixtures even when starting with a pure monomer, the resulting product containing polymers of varying chain length. The average molecular weight, molecular weight distribution, viscosities, boiling points, and other physical properties are readily controlled by known methods such as the adjustment of the conditions of hydrolysis and condensation, the kind and percentage of catalyst used, the diluent employed, the particular organo silicon compound being polymerized and pretreating and after treating processes.

The mineral oils which may be employed in carrying out the instant invention are well-known in the art. Preferred mineral oils for use in this invention are MARCOL 82 and 87 from Exxon Corporation.

The distillation process (either batch or continuous) is carried out in a well-known manner and, accordingly, need not be described in great detail. In general, conditions of temperature and pressure (preferably subatmospheric) employed in the process will be dependent upon the particular acid chloride being recovered and the other components of the distillation mass.

An "effective quantity" of distillation improvement additive is utilized for recovering the acid chloride from the mixture containing the acid chloride. The effective quantity of additive is that quantity of additive which will sufficiently fluidize the distillation mass to prevent polymerization and/or degradation of the acid chloride under the conditions of distillation and achieve the maximum recovery of acid chloride. The optimum amount being employed in any particular instance to achieve the maximum recovery of acid chloride can be readily determined by those skilled in the art. The optimum amount of additive employed will depend upon the particular acid chloride mixture being treated, the particular distillation improvement additive employed, and the conditions of distillation. It has been found that a range of from about 25% to about 300% based on the weight of the acid chloride in the mixture can be employed. A particularly preferred range is from about 50% to about 150%.

The process of this invention has been found particularly useful in recovering thiophene-2-acetyl chloride from the reaction mixture produced by the chlorination of alpha-thienylacetic acid with thionyl chloride.

It should be understood that the instant process is also applicable to the recovery of other acid chlorides produced by other reactions and from other components.

In the preferred embodiment of this invention, the distillation improvement additive is added directly to the reaction mixture resulting from the reaction of the acid with the chlorinating agent. The resulting mixture is then subjected to distillation. The residue remaining after distillation contains the additive by-products from chlorination and a minor quantity of the desired acid chloride. An advantage of this embodiment of the invention is that any non-volatile by-products present in the residue or produced during distillation remain in suspension or solution in the distillation improvement additive and are easily removed from the still in a fluid state.

Improved results can also be obtained by the addition of the distillation improvement additive to the residue remaining after the distillation of a major portion of the acid chloride and then continuing the distillation process.

The following examples are illustrative of the instant invention and are not to be regarded as limitative.

EXAMPLE 1

A 500-ml. flask was charged with 250 grams of a reaction mixture produced by the chlorination of alpha-thienylacetic acid with thionyl chloride. The distillation improvement additive (232 grams) was added to the flask. The distillation improvement additive utilized was SWS-101 (50) silicon fluid from SWS Silicon Corporation, Adrian, Michigan, SWS-101 (50) has the following properties:

Structure: A linear dimethyl polysiloxane terminated with nonreactive trimethyl-siloxy groups.
Viscosity: 50 centistokes at 25° C.
Specific Gravity: 0.963 at 25° C.
Volatility (wt. loss for 24 hours at 150° C.): 1%
Vapor Pressure: 0.01 mm. Hg at 25° C.

The contents of the flask were distilled at 5 mm. of Hg (absolute) and 89° C. (pot temperature). About 221 grams of substantially pure thiophene-2-acetyl chloride were produced in about 3 hours.

EXAMPLE 2

A 1000-ml. flask was charged with 400 grams of a reaction mixture produced by the chlorination of alpha-thienylacetic acid with thionyl chloride. The distillation improvement additive (369 grams) was added to the flask. The distillation improvement additive utilized was SWS-101 (50) silicon fluid.

The contents of the flask were distilled at 5 mm. of Hg (absolute) and 90° C. (pot temperature). About 362 grams of substantially pure thiophene-2-acetyl chloride were produced in about 3½ hours.

What is claimed:

1. A process for recovering an acid chloride having the structure:

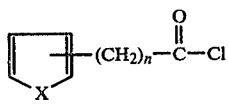

wherein X is a divalent oxygen or divalent sulfur atom, and n has the value 0, 1, 2, or 3, from a non-aqueous mixture containing the same, comprising distilling the acid chloride from the mixture in the presence of an effective quantity of a distillation improvement additive which is a mineral oil or an organopolysiloxane, wherein the distillation improvement additive remains substantially liquid under the conditions of distillation and the effective quantity of distillation improvement additive is from about 25% to about 300% based on the weight of the acid chloride.

2. The process of claim 1, wherein the distillation improvement additive is a mineral oil.

3. The process of claim 1, wherein the distillation improvement additive is an organopolysiloxane.

4. The process of claim 1, wherein the distillation is carried out at sub-atmospheric pressure.

5. The process of claim 1, wherein the acid chloride is thiophene-2-acetyl chloride.

6. The process of claim 2, wherein the acid chloride is thiophene-2-acetyl chloride.

7. The process of claim 3, wherein the acid chloride is thiophene-2-acetyl chloride.

* * * * *